(12) United States Patent
Shen et al.

(10) Patent No.: US 11,660,043 B2
(45) Date of Patent: May 30, 2023

(54) POSTURE DISPLAY METHOD, DEVICE AND SYSTEM OF GUIDING CHANNEL, AND READABLE STORAGE MEDIUM

(71) Applicant: HANGZHOU SANTAN MEDICAL TECHNOLOGY CO., LTD, Zhejiang (CN)

(72) Inventors: Liping Shen, Zhejiang (CN); Jianli Ning, Zhejiang (CN); Qi Xu, Zhejiang (CN); Xiao Chen, Zhejiang (CN)

(73) Assignee: HANGZHOU SANTAN MEDICAL TECHNOLOGY CO., LTD, Hangzhou (CN)

( * ) Notice: Subject to any disclaimer, the term of this patent is extended or adjusted under 35 U.S.C. 154(b) by 1209 days.

(21) Appl. No.: 16/132,617

(22) Filed: Sep. 17, 2018

(65) Prior Publication Data

US 2019/0350516 A1 Nov. 21, 2019

(51) Int. Cl.
  *G06F 3/01* (2006.01)
  *A61B 5/00* (2006.01)
  *A61B 5/11* (2006.01)
  *G01B 21/04* (2006.01)
  *G06T 19/20* (2011.01)
  *G06V 40/10* (2022.01)

(52) U.S. Cl.
  CPC .......... *A61B 5/4561* (2013.01); *A61B 5/1116* (2013.01); *G01B 21/04* (2013.01); *G06T 19/20* (2013.01); *G06V 40/11* (2022.01)

(58) Field of Classification Search
  CPC .......... G06F 19/18; G06F 19/24; G06F 19/20; G06F 19/16; G06G 19/22
  USPC .......................................................... 702/19
  See application file for complete search history.

(56) References Cited

U.S. PATENT DOCUMENTS

| | | | |
|---|---|---|---|
| 2003/0120183 A1* | 6/2003 | Simmons | A61F 4/00 600/595 |
| 2008/0249395 A1* | 10/2008 | Shachar | A61B 5/062 600/409 |
| 2018/0121728 A1* | 5/2018 | Wells | G16H 20/30 |

* cited by examiner

*Primary Examiner* — Gordon G Liu
(74) *Attorney, Agent, or Firm* — Dragon Sun Law Firm, PC; Nathaniel Perkins

(57) ABSTRACT

The present application relates to a posture display method, a device and a system for a guiding channel, and readable storage medium. The posture display method of a guiding channel includes determining an original position relation between a three-dimensional affected limb image and a virtual guiding channel displayed in a monitor according to an original position relation between the guiding channel and an affected limb and obtaining posture change data of the guiding channel. The method further includes adjusting the posture of the virtual guiding channel based on the posture change data, so as to the relative position relation between the virtual guiding channel and the three-dimensional affected limb image matches with the relative position relation between the guiding channel and the affected limb.

18 Claims, 7 Drawing Sheets

POSTURE DISPLAY METHOD, DEVICE AND SYSTEM OF GUIDING CHANNEL, AND READABLE STORAGE MEDIUM

CROSS-REFERENCE TO RELATED APPLICATIONS

This application is related to and claims priority to Chinese Patent Application Serial Number 2018104635740, filed May 16, 2018, and entitled Posture display method, device and system of guiding channel, and readable storage medium, the entirety of which is incorporated herein by reference.

BACKGROUND OF THE INVENTION

Field of the Invention

The present application relates to the medical technology field, especially to a posture display method, device and system, and readable storage medium.

Description of the Related Art

Currently, when securing an affected limb by a steel needle, the steel needle is usually needed to be inserted into the affected limb. The insertion process is not visible to the patient, which may cause anxiety and fear and even irresistible limb movements as the patient cannot understand the current status of the insertion process. This increases the difficulty of securing the limb and may be harmful for the health of the patient.

BRIEF SUMMARY OF THE INVENTION

The present application provides a posture display method, a device and a system of a guiding channel, and readable storage medium, to solve the technical problem. According to the first aspect of the embodiment of the present invention, a posture display method of guiding channel is provided. The method includes determining an original position relation between a three-dimensional affected limb image and a virtual guiding channel in a monitor according to an original position relation between the guiding channel and the affected limb; obtaining posture change data of the guiding channel; adjusting the posture of the virtual guiding channel based on the posture change data, so that a relative position relation between the virtual guiding channel and the three-dimensional affected limb image is matched to a relative position relation between the guiding channel and the affected limb.

Optionally, the determining of the original position relation between the three-dimensional affected limb image and the virtual guiding channel shown in the monitor according to the original position relation between the three-dimensional affected limb image and the virtual guiding channel in the monitor further includes determining coordinate information of the guiding channel in the absolute coordinate system according to coordinate information of the guiding channel in the reference coordinate system and a first conversion matrix between the reference coordinate system and the absolute coordinate system; determining the original position relation between the three-dimensional affected limb image and the virtual guiding channel according to coordinate information of the guiding channel in the absolute coordinate system and coordinate information of the three-dimensional affected limb image in the absolute coordinate system.

Optionally, the first conversion matrix is obtained through the following steps: determining standard two-dimensional coordinates of positioning marks on the guiding channel in the absolute coordinate system based on coordinate information of the positioning marks on the guiding channel in a preset projection plane and the conversion relation between an image coordinate system corresponding to the coordinate information and the absolute coordinate system; obtaining three-dimensional coordinates of the positioning marks in the reference coordinate system; establishing a functional relation between three-dimensional coordinates in the reference coordinate system, two-dimensional coordinates, and a second conversion matrix of the positioning marks, the second conversion matrix being used for indicating a conversion relation between the reference coordinate system and the absolute coordinate system; adjusting parameters contained in the second conversion matrix, and calculating corresponding two-dimensional coordinates to be matched based on the functional relation until the two-dimensional coordinates to be matched match the standard two-dimensional coordinates; and determining the first conversion matrix according to the parameters corresponding to the two-dimensional coordinates to be matched with the standard two-dimensional coordinates.

Optionally, the two-dimensional coordinates to be matched is determined to be matched with the standard two-dimensional coordinates when the two-norm between the two-dimensional coordinates to be matched and the standard two-dimensional coordinates is not greater than a preset threshold.

Optionally, the guiding channel keeps a contact status with a preset target spot in the affected limb, including: obtaining angle change data of the guiding channel relative to each coordinate axis of the reference coordinate system.

Optionally, the adjustment of the posture of the virtual guiding channel according to the posture change data further includes obtaining coordinate information of the guiding channel in the reference coordinate system after adjustment according to the angle change data and the original position information of the guiding channel in the reference coordinate system; determining the coordinate information of the guiding channel in the absolute coordinate system after adjustment according to the conversion relation between the coordinate information of the guiding channel in the reference coordinate system, the reference coordinate system and the absolute coordinate system after adjustment; and adjusting the posture of the virtual guiding channel according to the coordinate information of the guiding channel in the absolute coordinate system after adjustment.

Optionally, the number of the positioning marks is not less than four, with at least one mark of the positioning marks in a different plane from the others.

A posture display device of a guiding channel is provided according to the second aspect of the embodiment of the present application. Th posture display device of a guiding channel includes a determining module, which determines an original position relation between a three-dimensional affected limb image in a monitor and a virtual guiding channel according to an original position relation between the guiding channel and an affected limb; an obtaining module, which obtains posture change data of the guiding channel; and an adjusting module, which adjusts posture of the virtual guiding channel based on the posture change data, so as to match a relative position relation between the virtual guiding channel and the three-dimensional affected limb image to a relative position relation between the guiding channel and the affected limb.

According to the third aspect of the embodiment of the present application, a computer readable storage medium is provided, which stores computer instructions realizing steps of the method defined by any of the above embodiments when performed by a processor.

According to the fourth aspect of the embodiment of the present application, a posture display system of a guiding channel is provided. The posture display system of a guiding channel includes a guiding channel; and a display device connected to the guiding channel. The display device includes a display screen, which is used for showing virtual guiding channel and three-dimensional affected limb image. The posture display system of a guiding channel further includes a processor; and a memory for storing instructions executable by the processor; wherein the processor is configured to realize the steps of the method defined by any of the above embodiments.

The technical solution of the present application may include beneficial effects. In the present application, the posture of the virtual guiding channel relative to the three-dimensional affected limb image is adjusted according to the determined original position relation between the virtual guiding channel and the three-dimensional affected limb image and the posture change data of the guiding channel relative to the affected limb, so that the real-time posture of the guiding channel can be displayed on the monitor through the virtual guiding channel. This facilitates the patient to know the medical progress in time and eases their mood.

It shall be understood that the above general description and the details in the following part are only illustrative and cannot limit the present application.

DETAILED DESCRIPTION OF THE INVENTION

Figure 1:
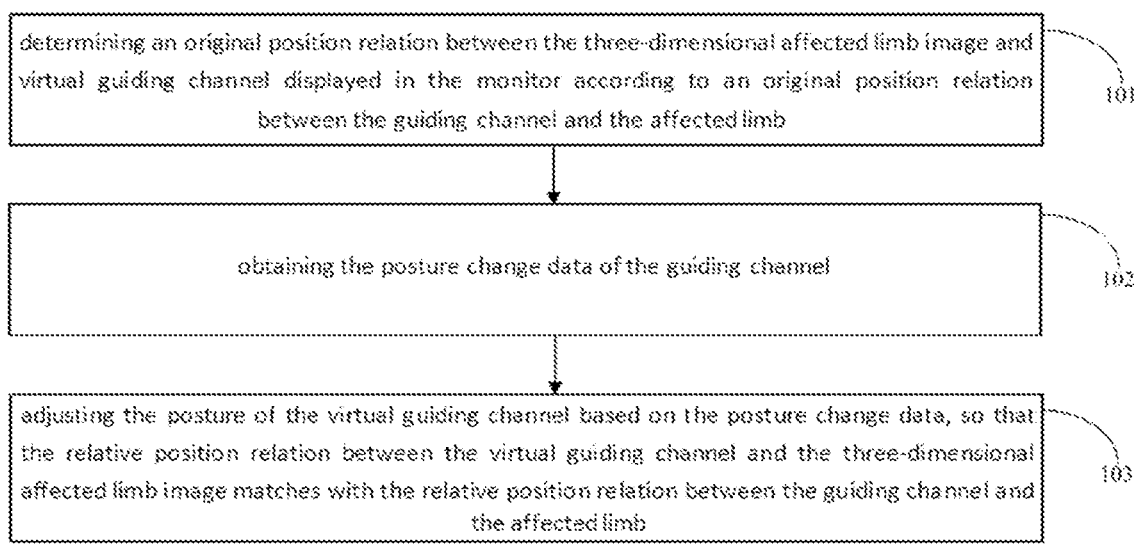
FIG. 1 is a flow chart for showing a posture display method of a guiding channel according to an exemplary embodiment.

Here the illustrative embodiments are described in details and shown in the drawings. When the following description refers to the drawings, unless otherwise noted, the same numbers in different drawings indicate the same or similar elements. The implementation methods in the following illustrative embodiments do not include all the ones consistent with the present application. On the contrary, they are only examples of devices and methods consistent with some aspects of the present application as detailed in the attached claims.

The terms used in the present application are only used for describing specific embodiments and not for limiting the present application. Unless otherwise noted, the words of single form with "a", "said", and "the" also include the plural forms in the present application and the attached claims. It shall also be understood that the term "and/or" in this description indicates one of the listed related items or any or all possible combinations thereof.

It shall be understood that although the present application may adopt terms such as first, second, and third to describe all kinds of information, the information shall not be limited to the terms, which are only used to distinguish information of the same type. For example, within the extent of the present application, the first information can be called the second information, and similarly, the second information can be called the first information. According to the context, the word "if" can be considered as "when" or "in response to".

FIG. 1 is a flow chart for showing a posture display method of a guiding channel according to an exemplary embodiment.

In the step 101, an original position relation between the three-dimensional affected limb image and virtual guiding channel displayed in the monitor is determined according to an original position relation between the guiding channel and the affected limb.

In the present embodiment, the guiding channel can guide an implant that is implanted in the affected limb. For example, when an angle of the guiding channel relative to the preset target spot on the surface of the bone in the affected limb is determined, the track of the implant that is implanted into the bone by the guiding channel can be determined. Assuming that the doctor implants the guiding channel into the affected limb at any angle and renders it in contact with the preset target spot, the original position relation between the three-dimensional affected limb image and the virtual guiding channel displayed in the monitor can be determined according to the original position relation between the guiding channel and the affected limb, and later posture adjustment can be conducted for the virtual guiding channel based on the original position relation.

The coordinate information of the guiding channel in the absolute coordinate system can be determined according to the coordinate information of the guiding channel in the reference coordinate system and the first conversion matrix between the reference coordinate system and the absolute coordinate system. The coordinate information of the guiding channel in the absolute coordinate system is that of the virtual guiding channel in the absolute coordinate system. Therefore, the original position relation between the three-dimensional affected limb image and the virtual guiding channel can be determined according to the coordinate information of the guiding channel in the absolute coordinate system and the coordinate information of the three-dimensional affected limb image in the absolute coordinate system.

The reference coordinate system is established based on the guiding channel, that is, based on the reference coordinate system, the coordinate information of each position on the guiding channel is known. The absolute reference system is established based on the three-dimensional affected limb image, that is, based on the absolute coordinate system, the coordinate information of each position of the three-dimensional affected limb image is known. Therefore, when the conversion relation between the absolute coordinate system and the reference coordinate system is determined, the coordinate information of the guiding channel in the absolute coordinate system can be determined, and further, the original position relation between the virtual guiding channel and the three-dimensional affected limb image can be determined.

Specifically, based on coordinate information of positioning marks on the guiding channel in a preset projection plane and the conversion relation between the absolute coordinate system and the image coordinate system corresponding to the coordinate information, the standard two-dimensional coordinates of the positioning marks in the absolute coordinate system are determined. The three-dimensional coordinates of the positioning marks in the reference coordinate system are obtained. The functional relation is established between three-dimensional coordinates of the positioning marks in the reference coordinate system, two-dimensional coordinates to be matched, and a second conversion matrix, the second conversion matrix being used for indicating the conversion relation between the reference coordinate system and the absolute coordinate system. Parameters contained in the second conversion matrix are adjusted, and corresponding two-dimensional coordinates to be matched are calculated based on the functional relation until the two-dimensional coordinates to be matched match the standard two-dimensional coordinates. The first conversion matrix is determined according to the parameters corresponding to the two-dimensional coordinates to be matched that match with the standard two-dimensional coordinates.

Further, the two-dimensional coordinates to be matched are determined to match with the standard two-dimensional coordinates when the two-norm between the two-dimensional coordinates to be matched and the standard two-dimensional coordinates is not greater than a preset threshold.

In the step 102, the posture change data of the guiding channel is obtained.

In this embodiment, when the posture of the guiding channel is adjusted, the contact between the guiding channel and the preset target spot on the bone surface in the affected limb can be always kept, so as to obtain the angle change data of the guiding channel relative to each coordinate axis of the reference coordinate system based on an angle sensor, that is, the posture of the guiding channel after adjustment can be obtained.

In the step 103, the posture of the virtual guiding channel is adjusted based on the posture change data, so that the relative position relation between the virtual guiding channel and the three-dimensional affected limb image matches with the relative position relation between the guiding channel and the affected limb.

In this embodiment, the posture change data can comprise the angle change data of the guiding channel relative to each coordinate axis of the reference coordinate system. According to the angle change data and the original position relation between the guiding channel and the affected limb, the coordinate information of the guiding channel after adjustment in the reference coordinate system is obtained. According to the coordinate information of the guiding channel after adjustment in the reference coordinate system and the conversion relation between the reference coordinate system and the absolute coordinate system, the coordinate information of the guiding channel after adjustment in the absolute coordinate system can be determined. Therefore, the posture of the virtual guiding channel can be adjusted according to the coordinate information of the guiding channel after adjustment in the absolute coordinate system. In this way, the relative position relation between the guiding channel and the affected limb matches the relative position relation between the virtual guiding channel and the three-dimensional affected limb image. That is, according to the relative position relation between the virtual guiding channel and the three-dimensional affected limb image displayed in the monitor, the relative position relation between the guiding channel and the affected limb can be known.

From the above embodiments, the present invention can, according to the determined original position relation between the virtual guiding channel and the three-dimensional affected limb image and the posture change data of the guiding channel relative to the affected limb, adjust the posture of the virtual guiding channel relative to the three-dimensional affected limb image, so as to display the real-time posture of the guiding channel on the monitor through the virtual guiding channel, which facilitates the patient to know the medical progress in time and eases their mood.

Figure 2:
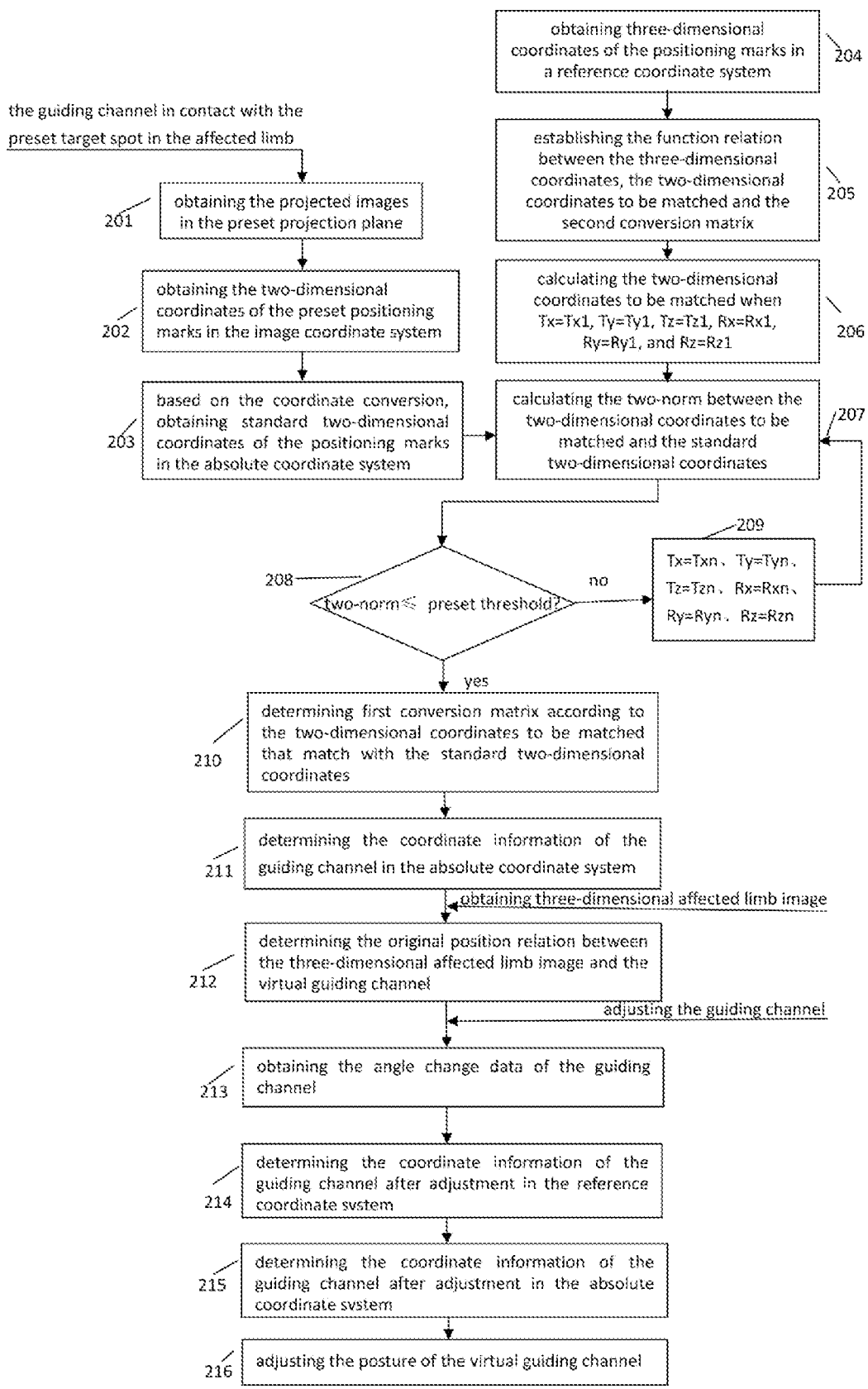
FIG. 2 is a flow chart for showing another posture display method of guiding channel according to an exemplary embodiment.

For a detailed explanation of the technical solution of the present application, description is given in combination with the specific operation process. FIG. 2 is a flow chart for showing another posture display method of guiding channel according to an exemplary embodiment. As shown in FIG. 2, the method can comprise:

In step 201, the projected images of the guiding channel and the affected limb in the preset projection plane are obtained.

In this embodiment, before obtaining the projected image in the preset projection plane, the guiding channel can be inserted into the affected limb first, and the end of the guiding channel is in contact with the preset target spot on the bone surface. The preset target spot can be determined by the medical staff, and implant positioned with the guiding channel can penetrate into the bone through the preset target spot for positioning the bone.

Figure 3A:
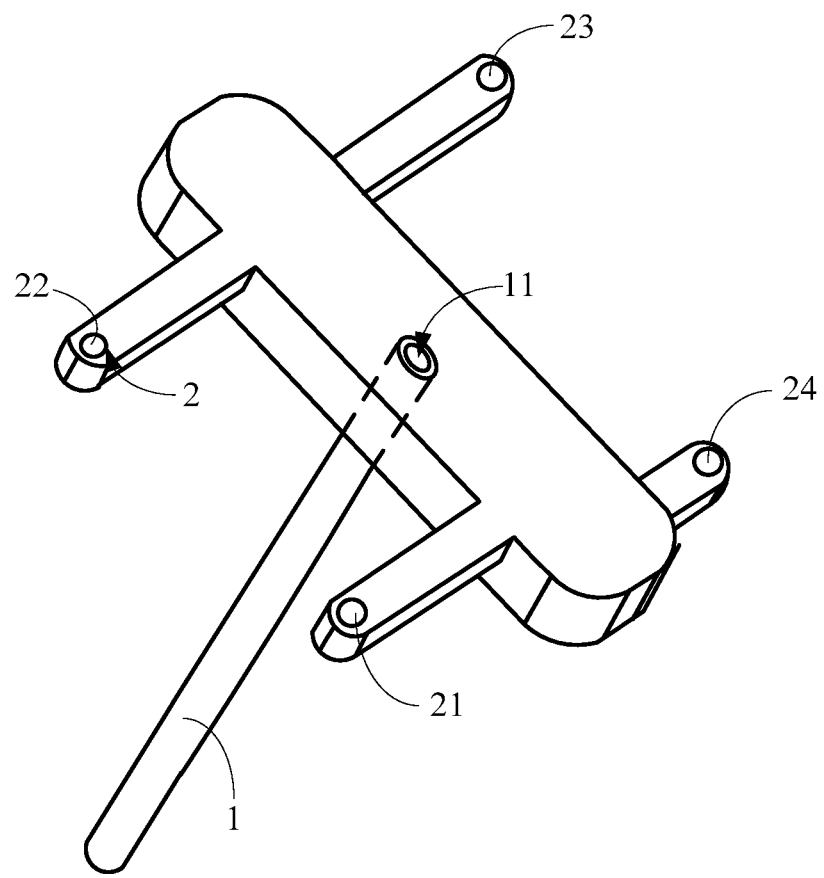
FIG. 3A is a structural diagram of a guiding channel according to an exemplary embodiment.

As shown in FIG. 3A, the guiding channel can comprise a holder 1, which comprises a hollow channel 11. One end of the hollow channel 11 can be used for the implant to go in, and the other end can be used for the implant to go out.

Figure 3B:
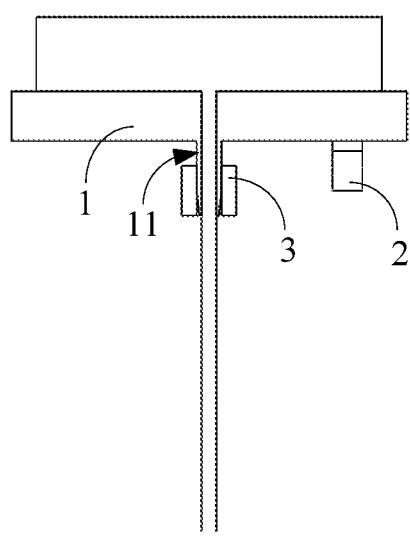
FIG. 3B is a structural diagram of another guiding channel according to an exemplary embodiment.

As shown in FIG. 3B, the guiding channel can further comprise a locking device 3, through which the implant and the holder 1 are connected detachably. For example, the locking device 3 can comprise a nut, which is rotated and screwed to fix the implant. Further, an elastomer is arranged on the inner wall of the hollow channel 11 at a position corresponding to the locking device 3. When the locking device 3 is tightened, the elastomer deforms and produces an acting force that acts upon the implant, and with the force it is abutted against the implant and alleviates the abrasion of the implant.

Figure 4:
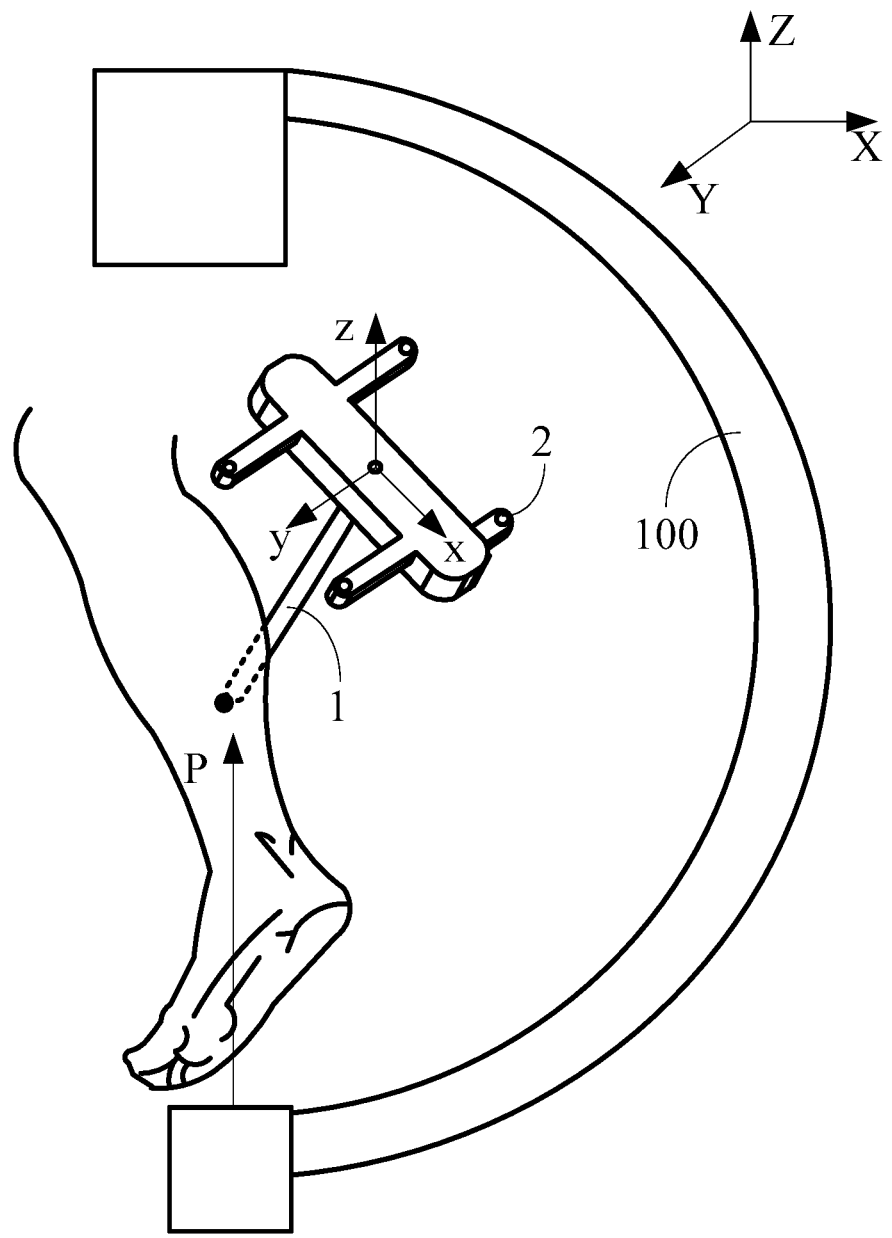
FIG. 4 is a posture schematic diagram for a guiding channel and an affected limb according to an exemplary embodiment.

The projected images of the guiding channel and the affected limb in the preset plane can be obtained through a medical projection apparatus. For example, as shown in FIG. 4, a C-arm machine 100 can emit a projection beam P towards the preset projection direction, so as to obtain two-dimensional images of the affected limb and the guiding channel in the preset projection plane perpendicular to the preset projection direction.

In step 202, the two-dimensional coordinates T_2d of the positioning marks on the guiding channel in the image coordinate system are obtained.

In this embodiment, the positioning marks are located on the guiding channel, and the relative position relation between the positioning marks and the holder 1 are fixed, wherein the number of the positioning marks is not less than four, and at least one of the at least four positioning marks is in a different plane from the other positioning marks, so that subsequently, each second conversion matrix can calculate two-dimensional coordinates to be matched accordingly. Detailed explanation is given to the second conversion matrix and the two-dimensional coordinates to be matched in the following part.

For example, the guiding channel can comprise at least four positioning balls 2, as shown in FIG. 3, including 21, 22, 23, and 24. The center of each positioning ball 2 corresponds to a positioning mark. Each positioning ball is located in a positioning seat of the guiding channel. Wherein the center of the positioning ball 23 is in a different plane from the center of the positioning ball 24; the centers of the positioning balls 21 and 22 are in the same plane, the centers of the positioning balls 21 and 22 are in a different plane from the center of the positioning ball 23, and the centers of the positioning balls 21 and 22 are in a different plane from the center of the positioning ball 24.

As shown in FIG. 4, an electronic apparatus may obtain the projected image of the C-arm machine 100 towards the preset projection direction and then obtain the two-dimensional coordinates T_2d of the positioning marks in the projected image; or the C-arm machine 100 may obtain the two-dimensional coordinates T_2d of the positioning marks in the projected image. Thereafter, the two-dimensional coordinates are sent to the electronic apparatus. This is not limited by the present application.

In step 203, based on the coordinate conversion relation between the image coordinate system and the absolute coordinate system XYZ, standard two-dimensional coordinates J_2d of the preset positioning marks in the absolute coordinate system XYZ are obtained.

In this embodiment, the conversion relation between the image coordinate system and the absolute coordinate system can be determined based on the projection direction P and the coordinate system of the C-arm machine 100. Assuming that the conversion relation between the image coordinate system and the absolute coordinate system can be represented by a matrix T1, the function between T1, T_2d, and J_2d can be represented as:

$$J\_2d=F1(T1,T\_2d);$$

wherein J_2d represents standard two-dimensional coordinates; T1 represents the conversion relation between the image coordinate system and the absolute coordinate system; and T_2d represents two-dimensional coordinates in the image coordinate system.

Therefore, a corresponding J_2d can be obtained based on the known T1 and T_2d.

In step 204, three-dimensional coordinates C_3d of the positioning marks in a reference coordinate system xyz are obtained.

In this embodiment, the reference coordinate system xyz can be established by the user based on the guiding channel, and in this reference coordinate system, the coordinate information of each position on the guiding channel is known, so that the three-dimensional coordinates C_3d of the positioning marks in the reference coordinate system xyz are determined.

In step 205, the function relation between the three-dimensional coordinates of the positioning marks in the reference coordinate system, the two-dimensional coordinates to be matched D_2d, and the second conversion matrix T2 is established.

In this embodiment, it can be assumed that the function relation between the two-dimensional coordinates to be matched D_2d and the second conversion matrix T2 is represented as:

$$D\_2d=F2(T2,C\_3d);$$

wherein D_2d represents the two-dimensional coordinates to be matched; T2 represents any conversion relation between the absolute coordinate system and the reference coordinate system; and C_3d represents the three-dimensional coordinate information of the preset marks in the reference coordinate system.

The second conversion matrix T2 can be used to indicate the conversion relation between the absolute coordinate system and the reference coordinate system, and since the two coordinate systems do not have deformation, the conversion between the two coordinate systems is a rigid conversion. That is, the reference coordinate system can be regarded as obtained after translation and rotation of the absolute coordinate system. Therefore, the second conversion matrix T3 can comprise six parameters: Tx, Ty, Tz, Rx, Ry, and Rz, wherein Tx represents offset relative to the X axis of the absolute coordinate system; Ty represents offset relative to the Y axis of the absolute coordinate system; Tz represents offset relative to the Z axis of the absolute coordinate system; Rx represents rotation amount relative to the X axis of the absolute coordinate system; Ry represents rotation amount relative to the Y axis of the absolute coordinate system; and Rz represents rotation amount relative to the Z axis of the absolute coordinate system.

In the step 206, the two-dimensional coordinates to be matched $D1\_2d$ is calculated when Tx=Tx1, Ty=Ty1, Tz=Tz1, Rx=Rx1, Ry=Ry1, and Rz=Rz1.

In step 207, the two-norm between the two-dimensional coordinates to be matched and the standard two-dimensional coordinates is calculated.

In step 208, it is determined whether the two-norm is not greater than the preset threshold.

In this embodiment, when the two-norm is not greater than the preset threshold, the process goes to step 210; and when the two-norm is greater than the preset threshold, the process goes to step 209.

Assuming that the parameters in T2 are as follows: Tx=Tx1, Ty=Ty1, Tz=Tz1, Rx=Rx1, Ry=Ry1, and Rz=Rz1, a two-dimensional coordinates to be matched D1_2d is calculated. Further, the two-norm E1 between the two-dimensional coordinates to be matched $D_1\_2d$ and the standard two-dimensional coordinates J_2d is calculated; if E1 is greater than the preset threshold, the process goes to step 208; otherwise, the process goes to step 210.

The preset threshold can be used to indicate the error between the actual conversion relation and the theoretical conversion relation between the absolute coordinate system and the reference coordinate system. For example, the preset threshold can be 0.01 or 0.001, which is not limited by the present application.

In step 209, the values of Tx, Ty, Tz, Rx, Ry, and Rz are adjusted, so that Tx=Txn, Ty=Tyn, Tz=Tzn, Rx=Rxn, Ry=Ryn, Rz=Rzn and For example, assuming that the two-norm E1 between the two-dimensional coordinates to be matched $D_1\_2d$ and the standard two-dimensional coordinates J_2d is greater than the preset threshold, the values of Tx, Ty, Tz, Rx, Ry, and Rz can be adjusted. For example, assuming n=2, that is, Tx=Tx2, Ty=Ty2, Tz=Tz2, Rx=Rx2, Ry=Ry2, and Rz=Rz2, the corresponding two-dimensional coordinates to be matched D2_2d can be calculated, and further the two-norm E2 between the two-dimensional coordinates to be matched D2_2d and the standard two-dimensional coordinates J_2d is calculated to determine whether E2 is greater than the preset threshold. Wherein the adjustment amount of Tx, Ty, Tz, Rx, Ry, and Rz can be determined according to the former calculation result, so that the obtained two-norms has a decreasing tendency. That is, the two-dimensional coordinates to be matched D_2d are increasingly closer to the standard two-dimensional coordinates J_2d.

In step 210, the first conversion matrix T3 is determined according to Tx, Ty, Tz, Rx, Ry, and Rz corresponding to the two-dimensional coordinates to be matched that match with the standard two-dimensional coordinates.

In this embodiment, assuming that when the parameters in T2 are as follows: Tx=Txm, Ty=Tym, Tz=Tzm, Rx=Rxm, Ry=Rym, and Ry=Rzm, the two-norm Em between the two-dimensional coordinates to be matched Dm_2d and the standard two-dimensional coordinates J_2d is not greater than the preset threshold. Then, the two-dimensional coordinates to be matched Dm_2d and the standard two-dimensional coordinates J_2d can be considered as matched with each other. Therefore, it can be determined that the first conversion matrix T3 contains parameters Txm, Tym, Tzm, Rxm, Rym, and Rzm, and the conversion relation between the absolute coordinate system and the reference coordinate system can be obtained.

It is noted that, in some other embodiments, the two-dimensional coordinates to be matched corresponding to each preset conversion matrix in a preset set is obtained; and then the two-norm between each two-dimensional coordinate to be matched and the standard two-dimensional coordinate is calculated. Then the first conversion matrix T3 is determined by comparing the two-dimensional coordinates to be matched corresponding to the smallest two-norm.

In step 211, the coordinate information of the guiding channel in the absolute coordinate system is determined according to the coordinate information of the guiding channel in the reference coordinate system and the first conversion matrix T3 between the reference coordinate system and the absolute coordinate system.

In step 212, the original position relation between the three-dimensional affected limb image and the virtual guiding channel is determined according to the coordinate information of the guiding channel and the three-dimensional affected limb image in the absolute coordinate system.

In this embodiment, the reference coordinate system is known, therefore the three-dimensional coordinate information of the marks on the guiding channel in the reference coordinate system can be obtained by measurement methods or other methods. According to the first conversion matrix between the absolute coordinate system and the reference coordinate system, the three-dimensional coordinate information of each point on the guiding channel in the absolute coordinate system can be obtained. Thereby, based on the three-dimensional coordinate information of each point on the guiding channel in the absolute coordinate system and the three-dimensional coordinate information of the three-dimensional affected limb image in the absolute coordinate system, the virtual guiding channel can be positioned in the absolute coordinate system, and the original position relation between the virtual guiding channel and the three-dimensional affected limb image in the absolute coordinate system can be determined. The three-dimensional affected limb image can be obtained through reconstruction after scanning with a CT apparatus or MR apparatus based on the absolute coordinate system, which is not limited by the present application.

In step 213, the angle change data of the guiding channel relative to each axis of the reference coordinate system based on the preset target spot is obtained.

Figure 5:
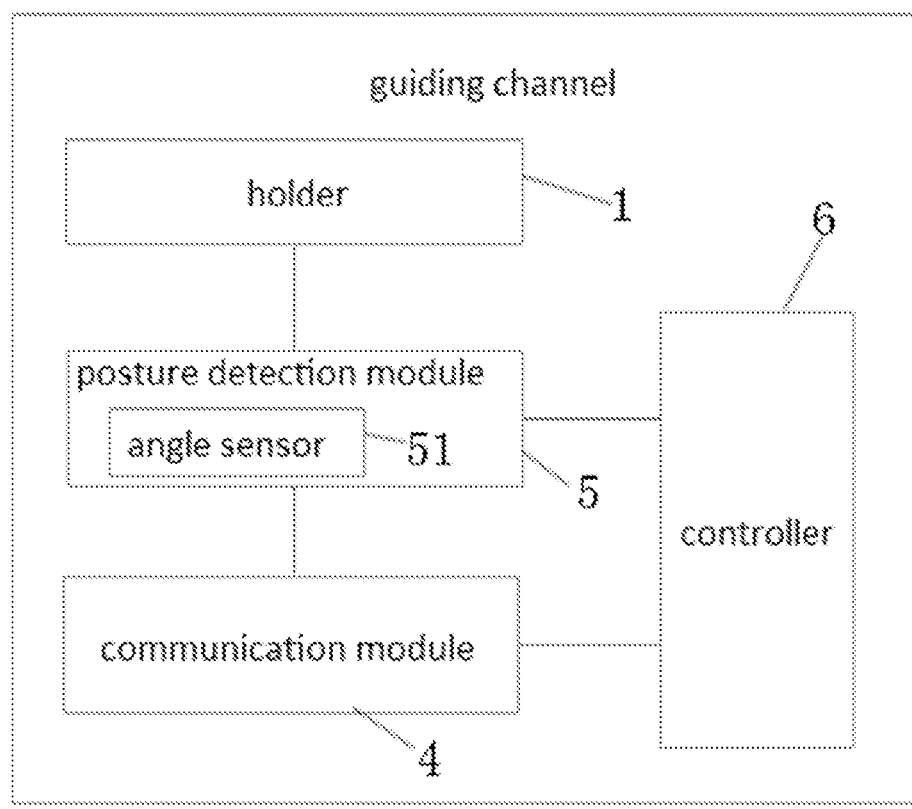
FIG. 5 is a structural block diagram of a guiding channel according to an exemplary embodiment.

In this embodiment, as shown in FIG. 5, the guiding channel can further comprise a communication module 4, a posture detection module 5, and a controller 6. The communication module 4 can be used to establish a communication connection between the guiding channel and external electronic apparatus. The communication module 4 can be a wireless transmission module, e.g. wife module, radio frequency module, or Bluetooth module, or the communication module 4 can be a wire transmission module, which may comprise an Ethernet interface module, Micro-USB interface module etc. This is not limited by the present application.

The posture detection module 5 can be used for detecting the posture change data of the guiding channel, which can be used for instructing the external electronic apparatus to adjust the posture of the virtual guiding channel, so that the relative position relation between the virtual guiding channel and the three-dimensional affected limb image matches the relative position relation between the guiding channel and the affected limb.

For example, the posture detection module 5 can comprise an angle sensor 51, the posture change data can comprise angle change data measured by the angle sensor 51. The angle change data being angle changes of the guiding channel relative to each coordinate axis of the reference coordinate system based on the preset target spot. Further, during adjustment, the end of the guiding channel always keeps in contact with the preset target spot in the affected limb, so that with the angle change data, the posture of the guiding channel after adjustment can be calculated, which facilitates simplification of the structure of the guiding channel and the calculation and increases the response efficiency.

The controller 6 can be in communication connection respectively with the communication module 4 and the posture detection module 5, so that through the controller 6, the detected posture change data can be sent to the external electronic apparatus. The controller 6 can perform modulation, filtering etc. for the posture change data, which is not limited by the present application.

In step 214, according to the angle change data and the original position relation between the guiding channel and the affected limb, the coordinate information of the guiding channel after adjustment in the reference coordinate system can be determined.

In this embodiment, assuming that the angle change data C={Rx, Ry, Rz}, wherein: Rx represents rotation of the guiding channel relative to the X axis of the reference coordinate system based on the preset target spot; Ry represents rotation of the guiding channel relative to the Y axis of the reference coordinate system based on the target spot; Rz represents rotation of the guiding channel relative to the Z axis of the reference coordinate system based on the target spot. As the angle change data C={Rx, Ry, Rz} and the original position relation between the guiding channel and the affected limb are known, the coordinate information of the guiding channel after adjustment in the reference coordinate system can be determined. For example, the function relation between the coordinate information of the guiding channel after adjustment in the reference coordinate system and the angle change data C={Rx, Ry, Rz} can be represented as:

$$D_{AR}=F3(C,D_O)$$

Wherein $D_{AR}$ represents coordinate information of the guiding channel after adjustment in the reference coordinate system; C represents angle change of the guiding channel relative to each coordinate axis of the reference coordinate system based on the preset target spot; $D_O$ represents original position information of the guiding channel in the reference coordinate system.

In step 215, according to the coordinate information of the guiding channel after adjustment in the reference coordinate system and the conversion relation between the reference coordinate system and the absolute coordinate system, the coordinate information of the guiding channel after adjustment in the absolute coordinate system is determined.

In this embodiment, according to the coordinate information $D_{AR}$ of the guiding channel in the reference coordinate system and the first conversion matrix T3 between the absolute coordinate system and the reference coordinate system, a function relation F4 is established as follows:

$$D_{AA}=F4(D_{AR},T3)$$

wherein T1 represents the first conversion matrix between the absolute coordinate system and the reference coordinate system determined in step 209; $D_{AR}$ represents coordinate information of the guiding channel after adjustment in the reference coordinate system; $D_{AA}$ represents coordinate information of the guiding channel after adjustment in the absolute coordinate system.

In step 216, according to the coordinate information of the guiding channel after adjustment in the absolute coordinate system, the posture of the virtual guiding channel is adjusted.

In this embodiment, according to the coordinate information $D_{AA}$ of the guiding channel after adjustment in the absolute system, the posture of the virtual guiding channel displayed in the monitor can be adjusted. Besides, as during adjustment of the guiding channel, the position and the posture of the affected limb are not changed relative to the reference coordinate system, that is the posture and the position of the three-dimensional affected limb image relative to the absolute coordinate system are not changed. Therefore, according to the coordinate information $D_{AA}$ of the guiding channel after adjustment in the absolute coordinate system, the position and the posture of the virtual guiding channel in the absolute coordinate system can be determined, and the relative position relation between the virtual guiding channel and the three-dimensional affected limb image and the relative position relation between the guiding channel and the affected limb can be rendered the same.

It shall be noted that when the posture of the affected limb needs to be changed in the actual process, the affected limb posture data can be obtained through the posture detection module for the affected limb, and with the affected limb posture data and the first conversion matrix T3 between the absolute coordinate system and the reference coordinate system, the affected limb posture in the absolute coordinate system can be determined. Then, according to the affected limb posture in the absolute coordinate system, the posture of the three-dimensional affected limb image displayed in the monitor can be adjusted, so as to keep the relative position relation between the affected limb and the guiding channel and the relative position relation between the three-dimensional affected limb image and the virtual guiding channel the same, which facilitates the user to check the treatment at any time and improves the user experience.

Figure 6:
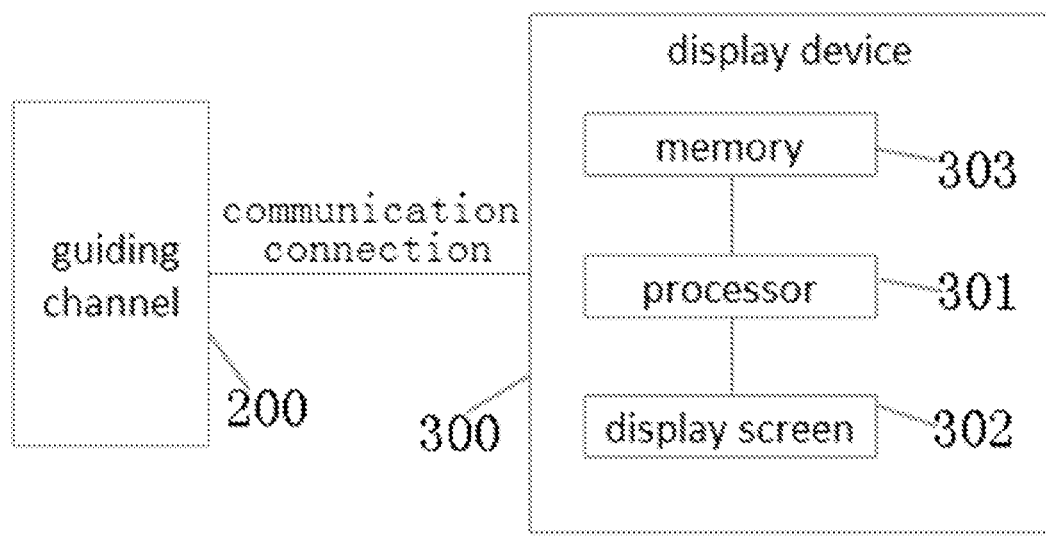
FIG. 6 is a posture display system block diagram of a guiding channel according to an exemplary embodiment.
Figure 7:
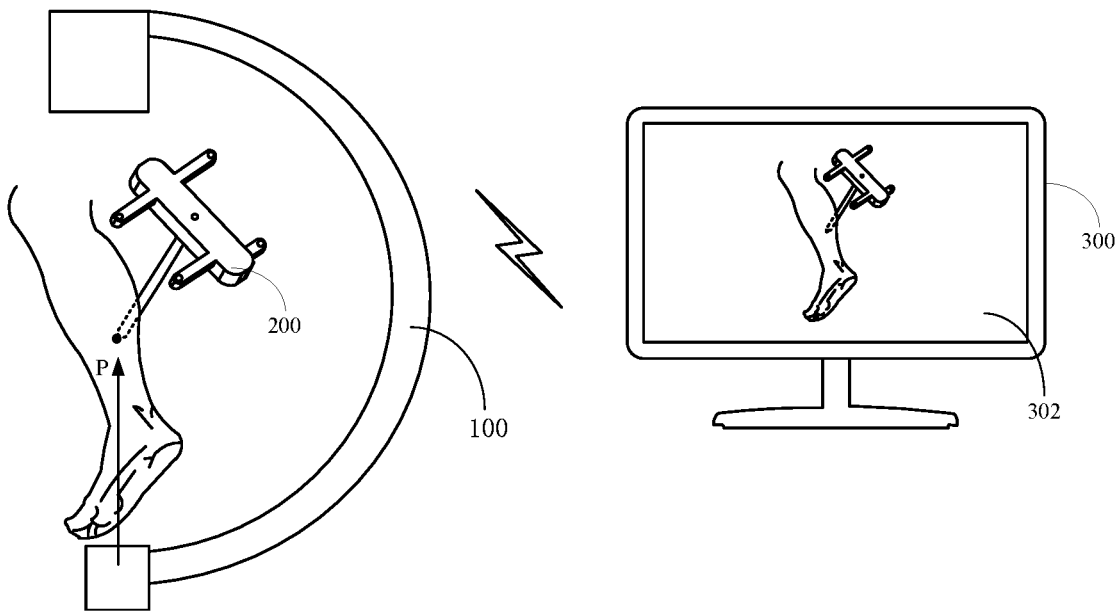
FIG. 7 is a posture display system schematic diagram of another guiding channel according to an exemplary embodiment.

Based on the technical solution of the present application, as shown in FIGS. 6 and 7, a posture display system of a guiding channel is provided. The posture display system can comprise a guiding channel 200 and a display device 300. The guiding channel can be structured as FIG. 3 or FIG. 4. The display device 300 can comprise a processor 301, a display screen 302, and a memory 303 for storing instructions executable by the processor 301. The display screen 302 can be used to display the virtual guiding channel and the three-dimensional affected limb image, and the processor 301 can be configured to realize the steps of the method of any of the above embodiments.

It shall be noted that: the display screen 302 can be assembled as one piece with the processor 301, e.g. mobile terminal or computer; or the display screen 302 and the processor 301 can be separated; for example, through the processor 301, the virtual guiding channel and the three-dimensional affected limb image can be projected to the display screen.

The posture display system can further comprise a photographing device, which can comprise a C-arm machine 100. The processor 301 is also used to obtain the coordinate information of the positioning marks in a preset projection plane by the C-arm machine 100, so as to obtain the standard two-dimensional coordinates of the positioning marks in the absolute coordinate system according to the coordinate information and the conversion relation between image coordinate system and absolute coordinate system, and establish a function relation between the two-dimensional coordinates to be matched, the second conversion matrix and the three-dimensional coordinates of the positioning marks in the reference coordinate system, until when the two-dimensional coordinates to be matched match with the standard two-dimensional coordinate, the corresponding second conversion matrix is determined as the first conversion matrix between the absolute coordinate system and the standard coordinate system, and according to the first conversion matrix, the original position relation between the virtual guiding channel and the three-dimensional affected limb image.

The posture change data comprises the reference angle change data of the guiding channel 200 relative to each coordinate axis of the reference coordinate system. The processor 301 is used to convert the reference angle data to absolute angle change data based on each coordinate axis of the absolute coordinate system according to the first conversion matrix, so as to adjust the posture of the virtual guiding channel according to the absolute angle change data.

Corresponding to the preceding embodiment of the posture display method, the present application further provides an embodiment of a posture display device.

Figure 8:
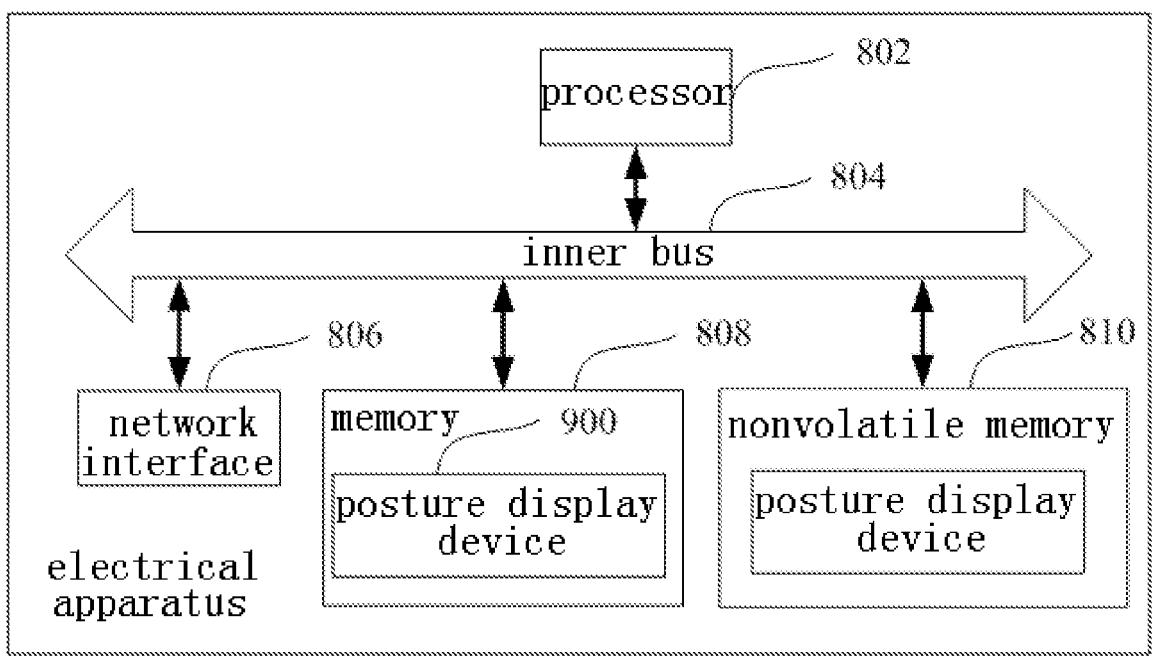
FIG. 8 is a schematic structural diagram of an apparatus provided according to an exemplary embodiment.

FIG. 8 is a schematic structural diagram of an apparatus provided according to an exemplary embodiment. Referring to FIG. 8, on the hardware level, the apparatus comprises a processor 802, an inner bus 804, a network interface 806, a memory 808, and a nonvolatile memory 810, and possibly other hardware required by the work. The processor 802 reads a corresponding computer program from the nonvolatile memory 810 to the memory 808 and then run it, and forms a posture display device 800 of a guiding channel on the logic level. Apart from the method of the software realization, the one or more embodiments of the present description do not exclude other realization methods, such as logic device or combination of software and hardware;

that is, the executive body of the following process is not limited to logic units and can also be hardware or logic device.

Figure 9:
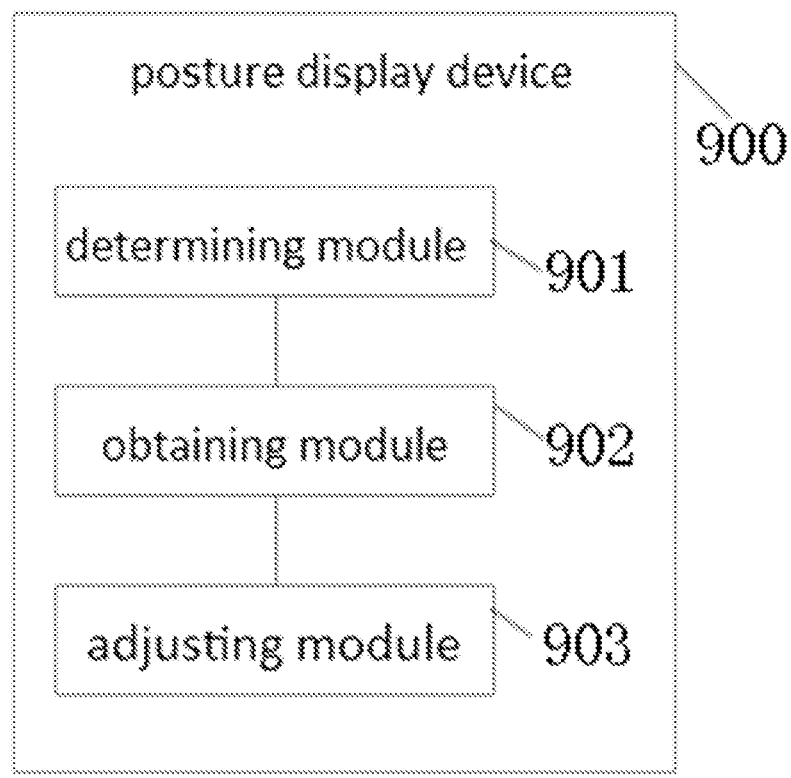
FIG. 9 is a block diagram for showing a posture display device of a guiding channel according to an exemplary embodiment.

As shown in FIG. 9, in the software implementation, the posture display device 900 of the guiding channel can comprise a determining module 901, an obtaining module 902, and an adjusting module 903.

The determining module 901 determines the original position relation between the three-dimensional affected limb image and the virtual guiding channel displayed in the monitor according to the original position relation between the guiding channel and the affected limb.

The obtaining module 902 obtains the posture change data of the guiding channel.

The adjusting module 903 adjusts the posture of the virtual guiding channel according to the posture change data, so that the relative position relation between the virtual guiding channel and the three-dimensional affected limb image matches the relative position relation between the guiding channel and the affected limb.

Optionally, the determining module 901 is used for: determining the coordinate information of the guiding channel in the absolute coordinate system according to the coordinate information of the guiding channel in the reference coordinate system and the first conversion matrix between the reference coordinate system and the absolute coordinate system; and determining the original position relation between the three-dimensional affected limb image and the virtual guiding channel according to the coordinate information of the guiding channel and the three-dimensional affected limb image in the absolute coordinate system.

The first conversion matrix is obtained with the following method: determining the standard two-dimensional coordinates of the positioning marks in the absolute coordinate system based on the coordinate information of the positioning marks on the guiding channel in the preset projection plane and the conversion relation between the absolute coordinate system and the image coordinate system corresponding to the coordinate information; obtaining the three-dimensional coordinates of the positioning marks in the reference coordinate system; establishing the function relation between the three-dimensional coordinates of the positioning marks in the reference coordinate system, the two-dimensional coordinates to be matched, and the second conversion matrix, the second conversion matrix is used for indicating the conversion relation between the reference coordinate system and the absolute coordinate system; adjusting the parameters contained in the second conversion matrix, and calculating the corresponding two-dimensional coordinates to be matched based on the function relation, until the two-dimensional coordinates to be matched match with the standard two-dimensional coordinates; and determining the first conversion matrix according to the parameters corresponding to the two-dimensional coordinates to be matched that match with the standard two-dimensional coordinates.

The determining module 901 is also used for: calculating the two-norm between the two-dimensional coordinates to be matched and the standard two-dimensional coordinates; and determining that the two-dimensional coordinates to be matched match with the standard two-dimensional coordinates when the two-norm is not greater than the preset threshold.

The guiding channel keeps a contact status with a preset target spot in the affected limb, and the obtaining module is used for: obtaining the angle change data of the guiding channel relative to each coordinate axis of the reference coordinate system.

The adjusting module 803 is used for: obtaining the coordinate information of the guiding channel after adjustment in the reference coordinate system according to the angle change data and the original position information of the guiding channel in the reference coordinate system; determining the coordinate information of the guiding channel after adjustment in the absolute coordinate system according to the coordinate information of the guiding channel after adjustment in the reference coordinate system and the conversion relation between the reference coordinate system and the absolute coordinate system; and adjusting the posture of the virtual guiding channel according to the coordinate information of the guiding channel after adjustment in the absolute coordinate system.

The number of the positioning marks is not less than four, with at least one of the positioning marks in a different plane from the others.

As to the device in the above embodiment, the specific operation method for each module is described in detail in the embodiment about the method, and no explanation will be given here.

For the device embodiment, as it corresponds to the method embodiment substantially, part of the method embodiment can be referred to for the associated parts. The device embodiment described in the above is only illustrative, and the units described as separate parts therein can be either physically separate or not; the parts shown as units can be either physical units or not; that is, they can be at one place, or distributed among a plurality of network units. Some or all the modules can be selected according to actual requirements to realize the technical solution of the present application, which can be understood and conducted by a person skilled in the art without inventive efforts.

The illustrative embodiment further provides a non-temporary computer readable storage medium containing instructions, e.g. a memory 810 comprising instructions. The above instructions may be executed by the processor 802 of the electronic apparatus to finish the above method. For example, the non-temporary computer readable storage medium can be ROM, RAM, CD-ROM, tape, floppy disk, and optical data memory.

After considering the description and applying the disclosure, a person skilled in the art could easily conceive of other implementations of the present application. The present application aims to cover any variation, use, or adaptive change, which comply with the general principle of the present application and include the common knowledge and conventional technical means in the art not disclosed by the present application. The description and embodiments are only illustrative, and the extent and spirit of the present application are pointed out by the following claims.

It shall be understood that the present application is not limited to the above described precise structure shown in the drawings and can have amendments and variations within the extent, which is defined only by the attached claims.

We claim:

1. A posture display method of a guiding channel, comprising:
    determining an original position relation between a three-dimensional affected limb image and a virtual guiding channel displayed in a monitor according to an original position relation between the guiding channel and an affected limb, wherein the determining the original position relation comprises determining coordinate information of the guiding channel in an absolute coordinate system according to coordinate information of the guiding channel in a reference coordinate system and a first conversion matrix T3 between the reference coordinate system and the absolute coordinate system, wherein the determining of the first conversion matrix T3 further comprises:
(1) determining standard two-dimensional coordinates of positioning marks on the guiding channel in the absolute coordinate system based on coordinate information of the positioning marks on the guiding channel in a preset projection plane and a conversion relation T1 between an image coordinate system corresponding to the coordinate information and the absolute coordinate system, wherein the conversion relation T1 between the image coordinate system and the absolute coordinate system is represented by a matrix T1, a first functional relation F1 between T1, T_2d, and J_2d is represented as:

$$J\_2d=F1(T1,T\_2d) \quad (1),$$

wherein J_2d represents standard two-dimensional coordinates; T1 represents the conversion relation between the image coordinate system and the absolute coordinate system; and T_2d represents two-dimensional coordinates in the image coordinate system;
(2) obtaining three-dimensional coordinates of the positioning marks in the reference coordinate system;
(3) establishing a second functional relation F2 between three-dimensional coordinates of the positioning marks in the reference coordinate system C_3d, two-dimensional coordinates to be matched D_2d, and a second conversion matrix T2, the second conversion matrix T2 being used for indicating a conversion relation between the reference coordinate system and the absolute coordinate system, wherein the second functional relation F2 between the two-dimensional coordinates to be matched D_2d and the second conversion matrix T2 is represented as:

$$D\_2d=F2(T2,C\_3d) \quad (2)$$

wherein D_2d represents the two-dimensional coordinates to be matched; T2 represents any conversion relation between the absolute coordinate system and the reference coordinate system; and C_3d represents the three-dimensional coordinate information of the preset marks in the reference coordinate system;
(4) adjusting parameters contained in the second conversion matrix T2, and calculating corresponding two-dimensional coordinates to be matched based on the second functional relation until the two-dimensional coordinates to be matched match with the standard two-dimensional coordinates, wherein the determining of the two-dimensional coordinates to be matched match with the standard two-dimensional coordinates occurs when a two-norm between the two-dimensional coordinates to be matched and the standard two-dimensional coordinates is less than a preset threshold; and
(5) determining the first conversion matrix T3 according to the parameters Tx, Ty, Tz, Rx, Ry, and Rz corresponding to the two-dimensional coordinates to be matched that match with the standard two-dimensional coordinates, wherein Tx represents offset relative to the X axis of the absolute coordinate system; Ty represents offset relative to the Y axis of the absolute coordinate system; Tz represents offset relative to the Z axis of the absolute coordinate system; Rx represents rotation amount relative to the X axis of the absolute coordinate system; Ry represents rotation amount relative to the Y axis of the absolute coordinate system; and Rz represents rotation amount relative to the Z axis of the absolute coordinate system;
obtaining posture change data of the guiding channel; and
adjusting a posture of the virtual guiding channel based on the posture change data, so the relative position relation between the virtual guiding channel and the three-dimensional affected limb image matches with the relative position relation between the guiding channel and the affected limb.

2. The posture display method according to claim 1, wherein the determining of the original position relation between the three-dimensional affected limb image and the virtual guiding channel displayed in the monitor according to the original position relation between the guiding channel and the affected limb further comprises:
determining coordinate information of the guiding channel in an absolute coordinate system according to coordinate information of the guiding channel in a reference coordinate system and a first conversion matrix between the reference coordinate system and the absolute coordinate system; and
determining the original position relation between the three-dimensional affected limb image and the virtual guiding channel according to the coordinate information of the guiding channel in the absolute coordinate system and the coordinate information of the three-dimensional affected limb image in the absolute coordinate system.

3. A posture display system of a guiding channel, comprising:
a guiding channel;
a display device connected to the guiding channel, comprising:
a display screen for displaying a virtual guiding channel and a three-dimensional affected limb image;
a processor; and
a memory for storing instructions executable by the processor; wherein the processor is configured to realize step of the method defined by claim 2.

4. The posture display method according to claim 1, wherein the guiding channel keeps a contact status with a preset target spot in the affected limb, and the obtaining the posture change data of the guiding channel further comprises:
obtaining angle change data of the guiding channel relative to each coordinate axis of the reference coordinate system.

5. The posture display method according to claim 4, wherein the adjusting of the posture of the virtual guiding channel according to the posture change data further comprises:
obtaining coordinate information of the guiding channel after adjustment in the reference coordinate system according to the angle change data and the original position information of the guiding channel in the reference coordinate system, wherein a third functional relation F3 between the coordinate information of the guiding channel after adjustment in the reference coordinate system and the angle change data C={Rx, Ry, Rz} is represented as:

$$D_{AR}=F3(C,D_O) \quad (3)$$

wherein $D_{AR}$ represents coordinate information of the guiding channel after adjustment in the reference coordinate system; C represents angle change of the guiding channel relative to each coordinate axis of the reference coordinate system based on the preset target spot; $D_O$ represents original position information of the guiding channel in the reference coordinate system;

determining the coordinate information of the guiding channel after adjustment in the absolute coordinate system according to the coordinate information of the guiding channel after adjustment in the reference coordinate system and the conversion relation between the reference coordinate system and the absolute coordinate system, wherein according to the coordinate information $D_{AR}$ of the guiding channel in the reference coordinate system and the first conversion matrix T3 between the absolute coordinate system and the reference coordinate system, a fourth functional relation F4 is established as follows:

$$D_{AA}=F4(D_{AR},T3) \quad (4)$$

wherein T3 represents the first conversion matrix between the absolute coordinate system and the reference coordinate system; $D_{AR}$ represents coordinate information of the guiding channel after adjustment in the reference coordinate system; $D_{AA}$ represents coordinate information of the guiding channel after adjustment in the absolute coordinate system; and adjusting the posture of the virtual guiding channel according to the coordinate information of the guiding channel after adjustment in the absolute coordinate system.

6. A posture display system of a guiding channel, comprising: a guiding channel;
a display device connected to the guiding channel, comprising;
a display screen for displaying a virtual guiding channel and a three-dimensional affected limb image;
a processor; and
a memory for storing instructions executable by the processor; wherein the processor is configured to realize step of the method defined by claim 5.

7. A posture display system of a guiding channel, comprising: a guiding channel;
a display device connected to the guiding channel, comprising;
a display screen for displaying a virtual guiding channel and a three-dimensional affected limb image;
a processor; and
a memory for storing instructions executable by the processor; wherein the processor is configured to realize step of the method defined by claim 4.

8. The posture display method according to claim 1, wherein the number of the positioning marks is not less than four, with at least one of the positioning marks in a different plane from the others.

9. A posture display system of a guiding channel, comprising:
a guiding channel;
a display device connected to the guiding channel, comprising;
a display screen for displaying a virtual guiding channel and a three-dimensional affected limb image;
a processor; and
a memory for storing instructions executable by the processor; wherein the processor is configured to realize step of the method defined by claim 8.

10. A posture display system of a guiding channel, comprising: a guiding channel;
a display device connected to the guiding channel, comprising;
a display screen for displaying a virtual guiding channel and a three-dimensional affected limb image;
a processor; and
a memory for storing instructions executable by the processor; wherein the processor is configured to realize step of the method defined by claim 1.

11. A posture display system of a guiding channel, comprising: a guiding channel;
a display device connected to the guiding channel, comprising;
a display screen for displaying a virtual guiding channel and a three-dimensional affected limb image;
a processor; and
a memory for storing instructions executable by the processor; wherein the processor is configured to realize step of the method defined by claim 1.

12. A posture display device of a guiding channel, comprising: a host computer with memory and at least one processor;
a determining module executing in the host computer, the determining module determining an original position relation between a three-dimensional affected limb image and a virtual guiding channel displayed in a monitor according to an original position relation between the guiding channel and an affected limb;
an obtaining module executing in the host computer, the obtaining module obtaining posture change data of the guiding channel; and
an adjusting module executing in the host computer, the adjusting module adjusting posture of the virtual guiding channel based on the posture change data, so as to match a relative position relation between the virtual guiding channel and the three-dimensional affected limb image with a relative position relation between the guiding channel and the affected limb.

13. A computer program product for posture display of a guiding channel, the computer program product including a computer readable storage medium having program instructions embodied therewith, the program instructions executable by a device to cause the device to perform a method including:
determining an original position relation between a three-dimensional affected limb image and a virtual guiding channel displayed in a monitor according to an original position relation between the guiding channel and an affected limb;
obtaining posture change data of the guiding channel; and
adjusting a posture of the virtual guiding channel based on the posture change data, so the relative position relation between the virtual guiding channel and the three-dimensional affected limb image matches with the relative position relation between the guiding channel and the affected limb.

14. The computer program product of claim 13, wherein the determining of the original position relation between the three-dimensional affected limb image and the virtual guiding channel displayed in the monitor according to the original position relation between the guiding channel and the affected limb further comprises:

determining coordinate information of the guiding channel in an absolute coordinate system according to coordinate information of the guiding channel in a reference coordinate system and a first conversion matrix between the reference coordinate system and the absolute coordinate system; and determining the original position relation between the three-dimensional affected limb image and the virtual guiding channel according to the coordinate information of the guiding channel in the absolute coordinate system and the coordinate information of the three-dimensional affected limb image in the absolute coordinate system.

15. The computer program product of claim 13, wherein the determining of the first conversion matrix further comprises:

determining standard two-dimensional coordinates of positioning marks on the guiding channel in the absolute coordinate system based on coordinate information of the positioning marks on the guiding channel in a preset projection plane and the conversion relation between an image coordinate system corresponding to the coordinate information and the absolute coordinate system;

obtaining three-dimensional coordinates of the positioning marks in the reference coordinate system;

establishing a functional relation between three-dimensional coordinates of the positioning marks in the reference coordinate system and a functional relation between two-dimensional coordinates to be matched and a second conversion matrix, the second conversion matrix being used for indicating a conversion relation between the reference coordinate system and the absolute coordinate system;

adjusting parameters contained in the second conversion matrix, and calculating corresponding two-dimensional coordinates to be matched based on the functional relation until the two-dimensional coordinates to be matched match with the standard two-dimensional coordinates; and determining the first conversion matrix according to the parameters corresponding to the two-dimensional coordinates to be matched that match with the standard two-dimensional coordinates.

16. The computer program product of claim 15, wherein the determining of the two-dimensional coordinates to be matched, match with the standard two-dimensional coordinates, when a two-norm between the two-dimensional coordinates to be matched and the standard two-dimensional coordinates is not greater than a preset threshold.

17. The computer program product of claim 13, wherein the guiding channel keeps a contact status with a preset target spot in the affected limb, and the obtaining the posture change data of the guiding channel further comprises:

obtaining angle change data of the guiding channel relative to each coordinate axis of the reference coordinate system.

18. The computer program product of claim 17, wherein the adjusting of the posture of the virtual guiding channel according to the posture change data further comprises:

obtaining coordinate information of the guiding channel after adjustment in the reference coordinate system according to the angle change data and the original position information of the guiding channel in the reference coordinate system;

determining the coordinate information of the guiding channel after adjustment in the absolute coordinate system according to the coordinate information of the guiding channel after adjustment in the reference coordinate system and the conversion relation between the reference coordinate system and the absolute coordinate system; and adjusting the posture of the virtual guiding channel according to the coordinate information of the guiding channel after adjustment in the absolute coordinate system.

\* \* \* \* \*